US012809043B2

(12) United States Patent
Goederer et al.

(10) Patent No.: US 12,809,043 B2
(45) Date of Patent: Nov. 24, 2026

(54) PHOTON-COUNTING X-RAY DETECTOR, METHOD FOR OPERATION OF A PHOTON-COUNTING X-RAY DETECTOR AND X-RAY DEVICE

(71) Applicant: Siemens Healthineers AG, Forchheim (DE)

(72) Inventors: Edgar Goederer, Forchheim (DE); Bodo Reitz, Forchheim (DE); Michael Hosemann, Erlangen (DE); Martin Hupfer, Erlangen (DE); Bjoern Kreisler, Hausen (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 78 days.

(21) Appl. No.: 19/077,242

(22) Filed: Mar. 12, 2025

(65) Prior Publication Data

US 2025/0291069 A1 Sep. 18, 2025

(30) Foreign Application Priority Data

Mar. 14, 2024 (EP) .................................... 24163527

(51) Int. Cl.

| | |
|---|---|
| ***G01T 1/17*** | (2006.01) |
| ***A61B 6/42*** | (2024.01) |
| ***G01T 1/24*** | (2006.01) |
| *A61B 6/03* | (2006.01) |

(52) U.S. Cl.

CPC .............. *G01T 1/17* (2013.01); *A61B 6/4233* (2013.01); *A61B 6/4241* (2013.01); *G01T 1/247* (2013.01); *A61B 6/032* (2013.01)

(58) Field of Classification Search

None

See application file for complete search history.

(56) References Cited

U.S. PATENT DOCUMENTS

| | | | |
|---|---|---|---|
| 2001/0025914 | A1 | 10/2001 | Pyyhtia et al. |
| 2012/0326049 | A1 | 12/2012 | Hannemann et al. |
| 2013/0028382 | A1 | 1/2013 | Spahn |

(Continued)

FOREIGN PATENT DOCUMENTS

| | | | |
|---|---|---|---|
| JP | 2011174936 | A | 9/2011 |
| WO | WO 2017054593 | A1 | 4/2017 |

OTHER PUBLICATIONS

Maj P et al.: "A Pixel Readout Chip in 40 nm CMOS Process for High Count Rate Imaging Systems with Minimization of Charge Sharing Effects", 2013, IEEE, USA.

*Primary Examiner* — Hoon K Song

(74) *Attorney, Agent, or Firm* — Harness, Dickey & Pierce, P.L.C.

(57) ABSTRACT

In a first signal processing stage of a photon-counting x-ray detector, each pixel element has a comparator and a monoflop unit with a delay unit. The comparator is configured to compare an electrical signal with a signal threshold value and provide a digital pixel signal to the monoflop unit. The monoflop unit is configured to provide a pulse signal with a defined pulse length based on the digital pixel signal. In a second signal processing stage, an output of the first signal processing stage is coupled, for signaling purposes, to a delay unit, which is configured to delay the pulse signal to obtain an adjusted pulse signal. A counting element is configured to count a counting signal based on the adjusted pulse signal.

20 Claims, 7 Drawing Sheets

(56) References Cited

U.S. PATENT DOCUMENTS

| | | | |
|---|---|---|---|
| 2014/0175299 A1 | 6/2014 | Spahn | |
| 2019/0025440 A1 | 1/2019 | Steadman Booker et al. | |
| 2021/0186439 A1 * | 6/2021 | Goederer | A61B 6/032 |
| 2021/0186440 A1 * | 6/2021 | Kreisler | A61B 6/4241 |
| 2022/0187478 A1 | 6/2022 | Hsieh | |
| 2024/0168179 A1 * | 5/2024 | Herrmann | G01T 1/17 |

* cited by examiner

PHOTON-COUNTING X-RAY DETECTOR, METHOD FOR OPERATION OF A PHOTON-COUNTING X-RAY DETECTOR AND X-RAY DEVICE

CROSS-REFERENCE TO RELATED APPLICATION(S)

The present application claims priority under 35 U.S.C. § 119 to European Patent Application No. 24163527.5, filed Mar. 14, 2024, the entire contents of which is incorporated herein by reference.

FIELD

One or more embodiments of the present invention relate to a photon-counting x-ray detector, to a method for operation of a photon-counting x-ray detector and to an x-ray device.

BACKGROUND

Photon-counting x-ray detectors are employed in many imaging applications. These x-ray detectors are thus used for example in computed tomography devices (CT devices) in medical imaging, in order to create a tomographic x-ray image of an examination region of an examination object, of a female or male patient for example.

In particular a photon-counting, direct-converting x-ray detector can be employed as a photon-counting x-ray detector. X-ray radiation arriving at the detector can be converted into electrical signals in such x-ray detectors by a suitable converter material. CdTe, CdZnTe, CdTeSe, CdZnTeSe, CdMnTe, GaAs, Si, Ge or other materials can be used as the converter material for example. Here x-ray photons, in particular x-ray quanta, can be absorbed in direct-converting converter material. In such cases one or more charge clouds can be created. When an emission of fluorescence photons occurs within the framework of an absorption process, these are mostly absorbed again according to a typical absorption length, for example appr. 100 μm in CdTe or CdZnTe, and create a further charge deposition there. The charge clouds are separated by an electrical field in the converter material and, on their way to pixel electrodes of pixel elements of the x-ray detector, influence an electrical signal in the pixel electrodes. A temporal course of the electrical signal at the pixel electrodes of the pixel elements depends in this case on a spatial position of the moving charges. Typically an electrical signal is influenced not just at a pixel electrode lying centrally below an absorption point of the x-ray quanta, but at the same time also at the neighboring pixel electrodes. The influenced electrical signal, in particular a signal pulse, can be amplified in each of the pixel elements and typically compared with a comparator threshold. If the signal pulse exceeds the comparator threshold, a counter result can be triggered. Depending on position and size of the charge clouds, the induced electrical signal can therefore also trigger a counter result in the neighboring pixel elements of the respective pixel element, even when the proportion of the charge deposited there is smaller. These counter events, in particular on a time scale of a few nanoseconds, occur simultaneously, therefore these coinciding counter events are also called coincidence counts.

A frequently widely used way of dealing with the problem of coinciding counter events is the normal registration of the counter events as if they were regular x-ray photons. Here it is therefore not the electrical signals of an x-ray spectrum, but actually the electrical signals of a pulse height spectrum that are detected. A charge sharing with the pixel elements adjacent to the respective pixel element in this case creates a "low-energy tailing", i.e. an additional count rate for lower energies that does not arise from low-energy x-ray photons. The fluorescence processes further often cause additional counter events with fluorescence energies as well as a corresponding underestimation of an energy of absorption events of higher energy concerned (K escape). Frequently the energy of the fluorescence photon is missing here and the primary counter event has a correspondingly lower signal height. Overall a disadvantageous contamination of the x-ray spectrum and an increase in noise thus occurs through the additional counter events. This causes an inferior separation capability, in particular a multi- or dual-energy resolution, as well as a suboptimal signal-to-noise ratio (SNR), a suboptimal contrast-to-noise ratio (CNR) and/or a suboptimal detective quantum efficiency (DQE).

A common countermeasure is analog charge summing. Here the simultaneously deposited electrical signals of neighboring pixel elements are summed and for example assigned to the pixel element contributing the most. The disadvantage of this solution, as well as the technical outlay, is the requirement for space and energy associated therewith, typically a considerably lengthening of a pulse width and/or dead time of the x-ray detector by a factor of between 10 and 100. The time until the next x-ray photon can be verified again without being disturbed by the previous counter event is thus increased markedly. Thus a x-ray flow is reduced reciprocally for which the spectral imaging can be used without disproportionate degradation by pile-up of consecutive signal pulses. This means that the analog charge summing solutions are primarily suitable for low x-ray photon flows and are not suitable for typical flows in a CT.

A further option is provided by anti-coincidence logic or coincidence inhibition logic. Here counter events that are registered simultaneously in neighboring pixel elements are blocked. For example a first pixel element that notices an electrical signal pulse can suppress the counting in neighboring pixel elements until it has finished processing the signal pulse. As an alternative or in addition a counter event can also be suppressed when counter events are identified in the neighboring pixel elements during the processing.

An example of this is given in the publication WO 2017/032548 A1. A disadvantage of such suppression is frequently that a number of counter events actually registered falls. In particular with a high signal flow, long dead times, pulse widths and/or shaping times and large pixel sizes, the result here can be a loss of the useful signal which is no longer negligible, in particular a complete loss.

SUMMARY

An object of one or more embodiments of the present invention is to specify a possibility for further improving the creation of x-ray imaging datasets, in particular while taking account of coincidences occurring.

At least this object is achieved in accordance with one or more embodiments of the present invention as claimed. Advantageous forms of embodiments with expedient developments are the subject matter of the subclaims.

Independent of the grammatical term usage of a specific person-related term, individuals with male, female or other gender identities should be included within the term.

Embodiments of the present invention relate, in a first aspect, to a photon-counting x-ray detector, which comprises a number of pixel elements and a converter element for conversion of x-ray radiation into electrical signals. In a first signal processing stage the pixel elements of the number of pixel elements each have at least one comparator and the number of pixel elements have at least one monoflop unit. The at least one comparator is embodied to compare the electrical signal with an energy source and, depending on the comparison, to provide a digital pixel signal to the at least one monoflop unit. The at least one monoflop unit is embodied, based on the digital pixel signal, to provide a pulse signal with a defined pulse length at an output of the first signal processing stage. In a second signal processing, the outputs of the first signal processing of the number of pixel elements are coupled for signaling purposes in each case to a delay unit. The respective delay unit is embodied to provide pulse signals with an adjusted delay in each case as adjusted pulse signals to a counting element in each case. In this case the respective adjusted delay is based on a circuit-related delay of the respective at least one pixel element of the pixel elements. The respective counting element is embodied to count a counting signal depending on the respective at least one adjusted pulse signal.

The photon-counting x-ray detector used within the framework of embodiments of the present invention can also be referred to as a direct-converting x-ray detector. Direct-converting x-ray detectors are mostly realized in a stack structure, in which, at a location of the converter material, i.e. on the converter element, an assigned evaluation unit is linked to the underside. The converter element can in particular comprise a converter material for converting x-ray radiation arriving at it into the electrical signal. The converter material can for example be CdTe, CdZnTe, CdTeSe, CdZnTeSe, CdMnTe, GaAs, Si, Ge or another suitable material. The use of CdTe can be especially advantageous. The underside of the converter element usually has a plurality of electrodes, also called sensor pixel electrodes, in the shape of a matrix, in the form of metallized contact elements. The evaluation unit is contacted with these for signaling purposes, for example soldered to them. Usually in this case a mating contact element designed in a pixel-shaped manner, also called the pixel electrode below, is opposite the converter-side contact element on the evaluation unit side. The evaluation unit then usually provides pixel electrodes for each pixel for the pixel-by-pixel processing of a signal entering via the pixel electrodes. X-ray radiation arriving is converted in the converter material of the converter element depending on the locally deposited energy of x-ray photons in charge carriers, based on which a signal, usually an electrical pulse, is created in the pixel-by-pixel pixel electronics, which is further processed. Pixel-by-pixel pixel electronics can be assigned a detection volume in the converter element, which is essentially embodied by the electrical field between a respective sensor pixel electrode and a top electrode, which is accommodated on the opposite side of the converter element and which forms the sensitive detection volume of a pixel element.

In accordance with an embodiment of the present invention, each pixel element of the number of pixel elements of the inventive photon-counting x-ray detector has a first, pixel-by-pixel signal processing stage. The pixel elements of the number of pixel elements, in the first signal processing stage, each have at least one comparator, in particular a number of comparators. The pixel elements of the number of pixel elements further have at least one monoflop unit in of the first signal processing stage. In this case the pixel elements of the number of pixel elements in the first signal processing stage can each have at least one monoflop unit. As an alternative, one or a number of pixel elements of the number of pixel elements in the first signal processing stage can have at least one, in particular shared or separate, monoflop unit.

The at least one comparator can be embodied in each case to compare the electrical signal provided by the converter element in an operating state of the x-ray detector with a signal threshold value. The x-ray detector can advantageously have an analog signal shaping chain, which can be embodied to shape and/or to amplify the electrical signal provided by the converter element and to provide it to the at least one comparator. The signal threshold value can in this case characterize an energy source. The signal threshold value can be embodied to detect a variable, for example an amplitude, of the electrical signal. If the signal threshold value is exceeded by the electrical signal the respective at least one comparator can provide the digital pixel signal in the operating state of the x-ray detector to the at least one monoflop unit. The term “comparator” is to be broadly interpreted within the framework of embodiments of the present invention. In particular a comparison element, which triggers an output signal when the set signal threshold value is exceeded by the incoming electrical signal is generally meant by this. The respective signal threshold value of the at least one comparator can be set to a fixed value. For example the respective signal threshold value can be permanently predetermined by the manufacturing of the at least one comparator. As an alternative the respective signal threshold value of the at least one comparator can be able to be changed or set. For example the respective signal threshold value can be able to be set to a plurality of fixed signal threshold values. As an alternative or in addition the respective signal threshold value can be able to be set within a range of signal threshold values. The at least one comparator can thus be embodied by the comparison to sort the respective electrical signal into an energy range, in particular an energy window.

If the first signal processing stage has a number of comparators, then the number of comparators can be embodied to provide a digital pixel signal to a common monoflop unit or to one monoflop unit in each case. There can essentially be a transition at the at least one comparator from the electrical, in particular analog, signal to at least one digital signal, in particular to the at least one digital pixel signal.

The first signal processing stage of a pixel element of the number of pixel elements can also have more than one comparator with a signal threshold value in each case, so that a number of digital pixel signals are able to be provided depending on the respective signal threshold values. In this case the comparators of the at least one pixel element of the number of pixel elements can advantageously have various signal threshold values that characterize various energy sources.

The at least one monoflop unit can comprise a monostable flip-flop, a monostable multivibrator and/or univibrator. The at least one monoflop unit can be embodied as a digital circuit that has precisely one stable state. The at least one monoflop unit can further be embodied to be triggered for a predefined period of time by an incoming signal, in particular the digital pixel signal, in the stable state. After the predefined period of time the at least one monoflop unit can return to the idle state. Advantageously the at least one monoflop unit can be embodied to be triggered by a change in the digital pixel signal, for example a rising flank of the digital pixel signal, in the stable state. The at least one monoflop unit can further be embodied, in the stable state, to provide the pulse signal with the defined pulse length. For this the monoflop unit can comprise a pulse signal generator for example. The defined pulse length can correspond to the predefined duration of the at least one monoflop unit. Advantageously the pulse signal can be able to be provided with a normalized pulse width via the at least one monoflop unit. In particular the respective pulse signal able to be provided by the at least one monoflop unit can be expressed as a length-normalized pulse signal.

Advantageously the outputs of the first signal processing stage of the number of pixel elements can be coupled for signaling purposes in the second signal processing stage to a delay unit, in particular connected to it. The coupling for signaling purposes can make it possible to forward the pulse signals provided at the outputs of the first signal processing stage to the delay units of the second signal processing stage.

Advantageously the second signal processing stage, at least for the respective pixel element, in particular for each output of the first signal processing stage, can have a delay unit in each case. The at least one delay unit can comprise a delay circuit that is embodied to provide the respective pulse signal with the respective delay as an adjusted pulse signal to the respective counting element. The at least one delay unit can be embodied for example for digital signal adjustment and/or for signaling purposes, in particular analog and/or digital, delay of the respective signal, in particular of the respective pulse signal. Thus the second signal processing stage for the respective pixel element, in particular for each of the number of pixel elements, can have at least one delay unit in each case.

The respective, in particular pixel-by-pixel, adjusted delay can be based on a circuit-related, in particular line-based, delay of the at least one pixel element of the number of pixel elements in each case, which is assigned to the respective delay unit. In particular the respective adjusted delay can be based on a difference between a highest value of a circuit-related, in particular line-related, delay of pixel elements of a group of pixel elements of the number of pixel elements and the circuit-related, in particular line-related, delay of the respective at least one pixel element of the group of pixel elements of the number of pixel elements which are assigned to the delay unit. This enables the pulse signals, at least of the group of pixel elements of the number of pixel elements, to be provided runtime-corrected to the respective counting element. In accordance with one form of embodiment the group of pixel elements can comprise each of the number of pixel elements, so that the pulse signals of all pixel elements of the number of pixel elements are able to be provided runtime-corrected to the respective counting element.

The adjusted pulse signals of the number of pixel elements can be able to be provided by the delay units to one counting element of the second signal processing stage in each case. As an alternative the adjusted pulse signals of the number of pixel elements can be able to be provided to a number of counting elements in each case. In particular the adjusted pulse signals of one of the pixel elements of the number of pixel elements can each be able to be provided to dedicated counting elements. As an alternative the adjusted pulse signals of a group of pixel elements of the number of pixel elements can be able to be provided to at least one common counting element.

The counting elements can each be embodied to count a counting signal depending on the respective at least one adjusted pulse signal, in particular on the respective number of adjusted pulse signals. In this case the respective counting signal can for example comprise a pixel counting signal or a coincidence counting signal. The counting elements can each be embodied, based on the at least one adjusted pulse signal arriving in an operating state of the x-ray detector, to increment a counter state of a counter by a counting unit, in particular on arrival of the at least one adjusted pulse signal within a predetermined amount of time. The counting elements can each comprise a plurality of counters. The counting elements can for example correspond to a resource block having a plurality of counters, so that, based on a number of signal outputs, a number of adjusted pulse signals provided are counted in each case and can be stored at least partly. The counting elements can each be embodied to provide the counting signal having information about the respective counter state of the at least one counter in each case.

The provision of the counting signals can comprise storage on a computer-readable storage medium and/or or display on a display unit and/or transfer to a provision unit. In particular a graphical representation of the counting signals, in particular a reconstruction of an x-ray image dataset based on the counting signals, can be able to be displayed via the display unit.

The proposed x-ray detector can make possible an improved creation of x-ray image datasets, in particular taking into account coincidences that occur. Through the pulse width normalization via the at least one monoflop unit for example a disproportionate degradation by pile-up of consecutive signal pulses can be reduced. Furthermore, the adjustment of the pulse signal by the at least one delay unit can make possible a runtime-corrected provision of the respective adjusted pulse signals for the respective counting elements. Through this an improved, in particular more precise, further processing of the signals provided at the outputs of the first signal processing stage can be made possible in the second signal processing stage, in particular with respect to a detection of coincidences.

In a further advantageous form of embodiment of the proposed x-ray detector the pixel elements in the first signal processing can further each have a signal amplifier. In this case the signal amplifier can be embodied to amplify the electrical signal and to provide the amplified electrical signal to the at least one comparator.

Advantageously the signal amplifiers can each have a signal input and a signal output. In an operating state of the x-ray detector the converter element can provide the electrical signal of the respective pixel element of the number of pixel elements to the signal input of the respective signal amplifiers. The signal amplifiers can each be embodied to amplify the respective electrical signal arriving, in particular to increase a signal value, for example a signal amplitude, and to provide the amplified electrical signal to the respective signal output, in particular to the at least one comparator. The signal amplifiers can further be embodied for shaping the electrical signal arriving.

The proposed form of embodiment can enable an improved signal processing of the electrical signal by the at least one comparator, the at least one monoflop unit.

In a further advantageous form of embodiment of the proposed x-ray detector the at least one monoflop unit can be embodied to provide the pulse signal on identification of a rising flank of the digital pixel signal.

The digital pixel signal can have various signal states, which can occur in a time sequence. The various signal states in this case can comprise a baseline, in particular if the signal threshold value is not exceeded in the at least one comparator, and an active state, in particular if the signal threshold value is exceeded in the at least one comparator. At transitions between the various signal states the pixel signal can have a flank, in particular a signal flank, in each case. At the transitions between a baseline state and an active state of the pixel signal the pixel signal can have a rising flank. At the transitions between an active state and a baseline state of the pixel signal the pixel signal can have a falling flank. Advantageously the at least one monoflop unit can be embodied to identify rising flanks in the respective pixel signal. The at least one monoflop unit can further be embodied to provide the pulse signal on identification of a rising flank, in particular only on identification of a rising flank of the digital pixel signal. In particular the monoflop unit can be embodied to be triggered by a rising flank of the digital pixel signal in the active state.

The proposed form of embodiment can make possible a reliable triggering of the respective pulse signal by the respective monoflop unit after conversion of an x-ray photon in the converter material.

In a further advantageous form of embodiment of the proposed x-ray detector, the pixel elements in the first signal processing stage can each have a number of comparators and a monoflop unit for each comparator. In this case the comparators of each of the number of pixel elements can be embodied to compare the electrical signal with various signal thresholds and to provide a digital pixel signal as a function of the comparison to the respective monoflop unit. The monoflop units can be embodied, based on the respective digital pixel signal, to provide a pulse signal with a defined pulse length to the respective output of the first signal processing stage in each case.

Advantageously the number of pixel elements in the first signal processing stage can each have a number of comparators, in particular the same number or a different number of comparators in each case, and a monoflop unit for each of the number of comparators. The comparators of each of the number of pixel elements can advantageously have various signal threshold values, which each correspond to a pixel-individual or pixel-combined, in particular coinciding, energy source. The comparators of each of the number of pixel elements can each be embodied to compare the electrical signal with its respective signal threshold value and to provide a digital pixel signal as a function of the comparison to the respective monoflop unit in each case. Pairs of the comparators of different pixel elements of at least one group of pixel elements of the number of pixel elements can advantageously have the same signal threshold values.

The monoflop units can be embodied, based on the respective digital pixel signal, in particular on identification of a rising flank of the digital pixel signal, to provide a pulse signal with a defined pulse length to the respective output of the first signal processing stage.

The proposed form of embodiment can advantageously make possible an improved energy-resolving creation of x-ray image datasets, in particular taking account of coincidences occurring.

In a further advantageous form of embodiment of the proposed x-ray detector, in the second signal processing stage, the delay units of at least one group of pixel elements of the number of pixel elements can be coupled for signaling purposes to a coincidence logic and to a counting element in each case. In this case the adjusted pulse signals of the at least one group of pixel elements can be able to be provided to the coincidence logic. The coincidence logic can be embodied to identify a coinciding occurrence of adjusted pulse signals of the number of pixel elements. The respective counting elements of the at least one group of pixel elements can be embodied to count a pixel-counting signal, which is based on a signal arriving directly in the pixel elements of the group of pixel elements, or to count a coincidence-counting signal on identification of a coincidence by the coincidence logic, which is based on a signal arriving directly in the respective pixel element and is based on the arriving coinciding signal of at least one further pixel element of the number of pixel elements.

Advantageously, in the second signal processing stage, the delay units of at least one group of pixel elements, in particular at least two pixel elements of the number of pixel elements, can be coupled, in particular connected, for signaling purposes to the coincidence logic and to at least one counting element in each case, in particular to a number of counting elements in each case. In the second signal processing stage in particular the delay units of a number, in particular of partly overlapping, groups of pixel elements, in particular of at least two pixel elements in each case, of the number of pixel elements can be coupled, in particular connected, for signaling purposes to a coincidence logic in each case and to at least one counting element, in particular to a number of counting elements.

Advantageously the at least one group of pixel elements in the second signal processing stage can have at least one first counting element, in particular a number of first counting elements, and at least one second counting element, in particular a number of second counting elements. The at least one first counting element can be embodied to count a pixel-counting signal, which is based on a signal arriving directly in the pixel elements of the group of pixel elements, in particular the pulse signal or the digital pixel signal. The at least one first counting element can be connected directly downstream of the respective delay unit of the respective pixel element of the at least one group of pixel elements.

The at least one second counting element can be embodied, on identification of a coincidence by the coincidence logic, to count a coincidence-counting signal, which is based on the signal arriving directly in the respective pixel element and on the coinciding arriving signal of at least one further pixel element of the number of pixel elements. The at least one second counting element can be connected directly downstream of the coincidence logic.

The counting elements of the second signal processing stage of the at least one group of pixel elements can be embodied switchable, in particular configurable, between a state as first or second counting element.

The coincidence logic can be embodied, on arrival of at least two coinciding signals occurring, in particular adjusted pulse signals, to provide an output signal, which is able to be counted as a coincidence-counting signal by a second counting element connected for signaling purposes to the coincidence logic. The coincidence logic can be embodied for example as an, in particular logical, coincidence tree and/or as an, in particular logical, coincidence circuit. In this case the coincidence logic can be connected directly downstream of the delay units of the at least one group of pixel elements.

The proposed form of embodiment can make possible an improved detection of coinciding counter events. The coincidence-counting signals provided can advantageously be used for correction of pixel-counting signals. The proposed form of embodiment can further be advantageous, in particular in the event of a high flow, since the coincidences, due to the defined pulse length of the respective adjusted pulse signals, are only able to be created in a time window around the first time that the threshold is exceeded.

In a further advantageous form of embodiment of the proposed x-ray detector, the second signal processing stage can have at least one first switching element, which is embodied to activate or to deactivate the coincidence logic. In this case the counting elements of the at least one group of pixel elements count the pixel-counting signal with a deactivated coincidence logic.

The first switching element can have a signal input and two signal outputs. Advantageously the signals, in particular the pulse signals or the digital pixel signals, can be able to be provided by the first signal processing stage of the at least one group of pixel elements to the signal input of the first switching element. The first switching element can be embodied to provide the signals arriving at its signal input optionally via its first signal output to the coincidence logic and via its second signal output to a first counting element in each case or only via its second signal output to a first counting element in each case. The first switching element can be switched over for example via a configuration (config bit). The first switching element can further comprise a combination of demultiplexer and multiplexer for activation or deactivation of the coincidence logic.

The proposed form of embodiment can make it possible to improve the testability of the circuit. Through this for example faulty circuits can already be identified during production of the x-ray detector and refinement losses can be minimized. Through this the creation of x-ray image datasets, in particular taking into account coincidences occurring, can moreover be improved.

In a further advantageous form of embodiment of the proposed x-ray detector the at least one group of pixel elements can comprise at least one of the pixel elements and at least one pixel element directly adjoining the pixel element in a row or column.

Advantageously the number of pixel elements can be arranged at least partly, in particular completely, in rows and/or columns, in particular in the form of a matrix, in relation to one another. Advantageously the at least one group of pixel elements can comprise at least one of the pixel elements of the number of pixel elements and at least on further pixel element, in particular a number of further pixel elements, which directly adjoins, in the form of rows or columns, the at least one pixel element, in particular is arranged directly adjacent to the at least one pixel element. Advantageously the at least one group of pixel elements can comprise the at least one pixel and all pixel elements directly adjoining it in the form of rows or columns, in particular directly adjoining it.

Advantageously, in the second signal processing stage, the delay units of a number of groups of pixel elements of the number of pixel elements can each be coupled to a coincidence logic and each to a counting element for signaling purposes. The number of groups of pixel elements of the number of pixel elements can at least partly comprise matching pixel elements as the at least one pixel element or the at least one further pixel element. In this case the number of groups of pixel elements can in particular overlap in the at least one pixel element or at least one of the at least one further pixel elements. For example the at least one further pixel element of a first group of pixel elements can be the at least one pixel element or the at least one further pixel element of a further group of a pixel elements. The at least one pixel element of a first group of pixel elements can further be the at least one further pixel element of a further group of pixel elements.

The proposed form of embodiment can enable a reliable identification of coinciding counter events.

In a further advantageous form of embodiment of the proposed x-ray detector, the x-ray detector can furthermore have a timing signal generation unit, which is embodied to provide a defined timing signal to the first and/or second signal processing stage. In this case the first and/or the second signal processing stage can be embodied to adjust their components, which are embodied for time-based processing and/or provision of the respective signals, with the aid of the timing signal.

The timing signal can be provided for example for calibrations, dead time measurements and/or to prevent a paralysis of a respective circuit of the first and/or second signal processing stage with high x-ray flows. The timing signal can be able to be provided as a clock signal for example. Through regular provision of a clock signal a signal can be registered at the corresponding component in the respective signal processing stage and thus an ability not to become paralyzed can be achieved. The timing signal can be provided to the first and/or second signal processing stage of at least one group of pixel elements of the number of pixel elements, in particular to the first and/or second signal processing stage of the number of pixel elements. The timing signal generation unit can have a number of sub timing signal generation units, which are embodied in each case to provide an, in particular dedicated, timing signal to one of the signal processing stages and/or to provide a component of the signal processing stages. The timing signal able to be provided by the timing signal generation unit can for example be able to be provided for a number, in particular all components, as the same, as different for different signal threshold values, pixel-individually or comparator-individually. The timing signal generation unit can further be able to be triggered for provision of the at least one timing signal by a rising or falling flank of the digital pixel signal. The timing signal generation unit can further be embodied to adjust a frequency of the timing signal able to be provided to a respective signal threshold value of the at least one comparator. The timing signal generation unit can further be embodied to provide the at least one timing signal with a defined delay, which suppresses a first clock for example.

The first and/or the second signal processing stage of the number of pixel elements can be embodied to adjust their respective components, in particular the at least one comparator and/or the at least one monoflop unit of the first signal processing stage and/or the at least one delay unit and/or the at least one counting element of the second signal processing stage with the aid of the timing signal. The adjustment of the respective components of the first and/or second signal processing stage based on the timing signal can comprise a calibration and/or synchronization.

The proposed form of embodiment can advantageously make possible a calibration and/or synchronization of the respective components of the first and/or second signal processing stage based on the timing signal, in particular for one or more, in particular for all, of the number of pixel elements.

In a further advantageous form of embodiment of the proposed x-ray detector, the first signal processing stage can have at least one second switching element, which is embodied to activate or to deactivate the at least one monoflop unit. In this case the at least one comparator, with a monoflop unit deactivated, can provide the digital pixel signal to the respective output of the first signal processing stage.

The second switching element can have a signal input and two signal outputs. Advantageously the at least one comparator in each case can provide the digital pixel signal at the signal input of the second switching element. The second switching element can be embodied optionally to provide the digital pixel signal via its first signal output to the at least one monoflop unit or via its second signal output to the respective output of the first signal processing stage. The second switching element can be switched over for example via a configuration (config bit). Advantageously the number of pixel elements in the first signal processing stage can each have a second switching element, in particular a second switching element in each case for each comparator of the at least one comparator. The second switching element can further comprise a combination of demultiplexer and multiplexer for activation or deactivation of the at least one monoflop unit.

The proposed form of embodiment can enable an optional deactivation of the at least one monoflop unit. What can be advantageously achieved through this is that a time window open for a registration of coinciding counter events depends on a deposited pulse height, in particular a period of time during which the respective signal threshold value of the respective comparator is exceeded, in the respective pixel element. Through this the pixel elements in which the most charge is deposited during an event are given a longer coincidence window than pixel elements with only smaller charge deposition. As a consequence the coinciding counter event can advantageously be registered with high probability in the pixel elements with the greatest charge deposition. This can improve a spectral local resolution, since the coincidence-counting signal is thus localized more clearly and correctly, in particular as regards a location of the primary charge deposition.

The option of choice as regards the use of the monoflop enables the proposed circuit advantageously to be adapted to the adapted digital pixel signal. In the case of a low flow an increased spectral local resolution can be advantageous. In pile-up dominated measurements on the other hand a shortening able to be achieved by the monoflop unit of an interval sensitive to coincidence and/or a faster re-triggering ability of counter events can advantageously be used for a reduction of a flow-dependent degradation of the coincidence-counting signal.

In a further advantageous form of embodiment of the proposed x-ray detector the first signal processing stage can have at least one third switching element, which is embodied to activate and/or deactivate the delay unit. Advantageously, on deactivation of the at least one delay unit, the signal provided to the respective delay unit of the at least one delay unit can be able to be provided to the respective counting element.

The third switching element can have a signal input and two signal outputs. Advantageously the respective monoflop unit can provide the pulse signal to the signal input of the third switching element. If the first signal processing stage has at least one second switching element, in a first operating state, in particular a first state of the second switching element, the respective monoflop unit can provide the pulse signal via the first signal output of the second switching element to the signal input of the third switching element. In a second operating state, in particular a second state of the second switching element, the respective comparator can provide the digital pixel signal via the second signal output of the second switching element to the signal input of the third switching element. The third switching element can be embodied optionally to provide the signal arriving at its signal input, in particular the pulse signal or the digital pixel signal, via its first signal output to the delay unit or via its second signal output to the respective counting element. The third switching element can be switched over for example via a configuration (config bit). Advantageously the number of pixel elements in the first signal processing stage can each have a third switching element, in particular a third switching element for each delay unit in each case. The at least one third switching element can further comprise a combination of demultiplexer and multiplexer for activation or deactivation of the respective delay unit.

The proposed form of embodiment can make it possible to improve the testability of the circuit. Through this the creation of x-ray image datasets, in particular taking account of coincidences occurring, can moreover be further improved.

In a further advantageous form of embodiment of the proposed x-ray detector the defined pulse length of the pulse signal able to be provided by the at least one monoflop unit can be able to be adjusted, in particular between 1 ns and 20 ns, and/or the delay of the adjusted pulse signal able to be provided by the at least one delay unit.

Advantageously the defined pulse length of the pulse signal able to be provided by the at least one monoflop unit, can in particular be able to be adjusted, in particular set. In particular the defined pulse lengths of pulse signals able to be provided by the number of monoflop units overall or individually, can be able to be adjusted, in particular at least in groups. Advantageously the defined pulse length of the pulse signal able to be provided by the at least one monoflop unit can be able to be adjusted to a value of 1 ns to 20 ns.

As an alternative or in addition, the delay of the adjusted pulse signal able to be provided by the at least one delay unit can be able to be adjusted, in particular set. In particular the delays of the adjusted pulse signals able to be provided as a whole or individually by the number of delay units, in particular at least in groups, can be able to be adjusted. For example the at least one delay unit can provide the respective pulse signal to the respective counting element with an additional, in particular pixel-independent, delay.

The x-ray detector can advantageously have a setting element, for example a switch, and/or an input unit, for example a keyboard, which are embodied to adjust the defined pulse length of the pulse signal able to be provided by the at least one monoflop unit and/or the delay of the adjusted pulse signal able to be provided by the at least one delay unit, in particular to increase it or reduce it.

The adjustability of the defined pulse length and delay can advantageously make it possible to reduce the runtime differences between various pixel elements, so that a shorter and thus advantageous defined pulse length is able to be set. With fixed defined pulse lengths these can either be too short or too long. With a defined pulse length that is too short the result can be a loss of coinciding counter events. With a defined pulse length that is too long, a signal quality in the case of higher flows can be suboptimal. Advantageously the adjustability of the defined pulse length can make it possible to avoid these two cases, in particular a defined pulse length that is too short or too long.

In a second aspect, embodiments of the present invention relate to a method for operating a proposed photon-counting x-ray detector. In a first step a) x-ray radiation is received with the photon-counting x-ray detector. In this case the x-ray radiation is converted by the converter element into electrical signals. In a second step b) the electrical signals created are processed by the first signal processing stage and the second signal processing stage of the photon-counting x-ray detector. In this case pulse signals are provided to the outputs of the first signal processing stage, which are further processed by the second signal processing stage. In a third step c) the counting signals of the counting elements are provided to the second signal processing stage.

The advantages of the method essentially correspond to the advantages of the proposed photon-counting x-ray detector. Features, advantages, or alternate forms of embodiment mentioned here can likewise by transferred to the other claimed subject matter and vice versa.

The receiving of the x-ray radiation in step a) can comprise the conversion of the x-ray radiation by the converter element into electrical signals and the provision of the electrical signals to the at least one comparator of the first signal processing stage of the pixel elements of the number of pixel elements.

The provision of the counting signals can comprise storage on a computer-readable storage medium and/or display on a display unit and/or transfer to a provision unit. In particular a graphical representation of the counting signals, in particular a reconstruction based on the counting signals, can be able to be shown via the display unit.

In a further advantageous form of embodiment of the proposed method an x-ray image dataset can be created based on the counting signals provided.

The creation of the x-ray image dataset can comprise a reconstruction of image values, in particular voxel values or pixel values, based on the counting signals, in particular of a number of the counting signals for each pixel element. In particular the image values of the x-ray image dataset can be reconstructed based on the pixel-counting signals, in particular on a number of the pixel-counting signals. The respective pixel-counting signals, in particular the respective numbers of pixel-counting signals, can further be corrected, in particular adjusted, based on the respective coincidence-counting signals, in particular respective numbers of the coincidence-counting signals. For example the respective number of coincidence-counting signals can be subtracted pixel-by-pixel from the respective number of pixel-counting signals. For example a weighted subtraction can be provided, in particular in that before the subtraction a mixing factor is multiplied by the number of coincidence-counting signals. This means that only a proportion or a multiple of the at least one number of coincidence-counting signals can be subtracted or added.

In a further advantageous form of embodiment of the proposed method, a check can be made in step c) as to whether the counting signal has a coincidence-counting signal. If it does not, the defined pulse length can be increased and the steps a) to c) can be repeated. If it does, and with no previous enlargement of the defined pulse length, the defined pulse length can be reduced and the steps a) to c) repeated. Otherwise the method can be ended.

The checking as to whether the counting signal has a coincidence-counting signal can for example comprise a comparison of a counter state of the coincidence-counting element before the beginning of the method, in particular before the moment of the execution of the steps a) to c), with a counter state of the coincidence-counting element at that moment. An increase in the counter state of the coincidence-counting element can be identified as the presence of a coincidence-counting signal. An unchanged counter state of the coincidence-counting element can be identified as the absence of a coincidence-counting signal.

With a negative outcome, in particular in the absence of a coincidence-counting signal, the defined pulse length can be increased, for example by a predetermined change value. The steps a) to c) can further be repeated if the answer is no.

With a positive outcome, in particular if a coincidence-counting signal is present, a further check can be made as to whether the steps a) to c) have been repeated and whether the defined pulse length has been increased in the previous execution of the steps a) to c). If it has, i.e. if a coincidence-counting signal is present and there has been previous enlargement of the defined pulse length, the method can be ended. If a coincidence-counting signal is present and there has not been any previous enlargement of the defined pulse length, the defined pulse length can be reduced, for example by the predetermined change value or by a further predetermined change value, and the steps a) to c) can be repeated.

Advantageously the defined pulse length can be optimized, in particular minimized, by this, wherein it can be ensured that coincidence-counting signals are able to be detected via the optimized defined pulse length. The proposed form of embodiment can be considered as tuning the defined pulse length in such a way that coincidences are able to be reliably triggered by the respective pulse signals. Through this, a probability of additional coincidences being falsely triggered by pulse lengths of the respective pulse signals that are too long can be reduced and a signal quality can thus be optimized.

Embodiments of the present invention relate in a third aspect to an x-ray device, comprising an x-ray source and a proposed photon-counting x-ray detector. In this case the x-ray source is embodied to emit x-ray radiation for illumination of the x-ray detector.

The advantages of the proposed x-ray device essentially correspond to the advantages of the proposed photon-counting x-ray detector. Features, advantages, or alternate forms of embodiment mentioned here can likewise by transferred to the other claimed subject matter and vice versa.

The x-ray source and the x-ray detector can advantageously be arranged in a defined arrangement in relation to one another. The defined arrangement of x-ray source and x-ray detector can further be supported movably, in particular able to be rotated and/or translated, for example in relation to an examination object to be imaged. The x-ray source can be embodied to emit x-ray radiation for illumination of the x-ray detector. The x-ray detector can be embodied to convert the x-ray radiation arriving, for example after an interaction with the examination object, into electrical signals by the converter element.

Advantageously the x-ray device can be embodied as a Computed Tomography device (CT device) and/or C-arm x-ray device and/or O-arm x-ray device.

BRIEF DESCRIPTION OF THE DRAWINGS

Exemplary embodiments of the present invention are shown in the drawings and will be described in greater detail below. The same reference characters are used in different figures for the same features. In the figures.

DETAILED DESCRIPTION

Figure 1:
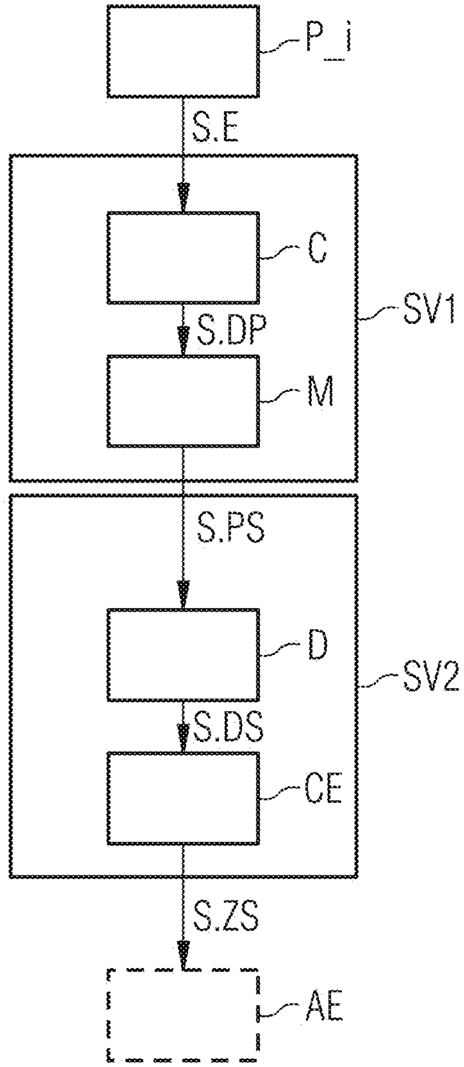
FIGS. 1, 2, 3, 4, 5 and 6 show schematic diagrams of various advantageous forms of embodiment of a proposed photon-counting x-ray detector.

FIG. 1 shows a schematic diagram of an advantageous form of embodiment of a proposed photon-counting x-ray detector. The x-ray detector can comprise a number of pixel elements and a converter element for conversion of x-ray radiation into electrical signals S.E. In a first signal processing stage SV1 a respective pixel element P_i of the number of pixel elements can have at least one comparator C and the number of pixel elements can have at least one monoflop unit M. The at least one comparator C can be embodied to compare the electrical signal S.E with a signal threshold value and to provide a digital pixel signal S.DP depending on the comparison to the at least one monoflop unit M. The at least one monoflop unit M can be embodied, based on the digital pixel signal S.DP, to provide a pulse signal S.PS with a defined pulse length to an output of the first signal processing stage SV1. In a second signal processing stage SV2 the outputs of the first signal processing stage of the number of pixel elements, in particular of the respective pixel element P_i, can each be coupled for signaling purposes to a delay unit D. The respective delay unit D can be embodied to provide the pulse signals S.PS with an adjusted delay in each case as adjusted pulse signal S.DS to a counting element CE in each case. In this case the respective adjusted delay can be based on a circuit-related delay of the respective at least one pixel element P_i of the number of pixel elements. The respective counting element CE can be embodied to count a counting signal S.ZS depending on the respective at least one adjusted pulse signal S.DS. The at least one counting element CE can be embodied to provide the counting signal S.ZS to an evaluation unit AE. The optional evaluation unit AE can for example comprise a digital processing chain, in particular for calculation, processing and/or evaluation of the respective counting signal S.ZS.

Advantageously the at least one monoflop unit M can be embodied to provide the pulse signal S.PS on identification of a rising flank of the digital pixel signal S.DP. Advantageously the defined pulse length of the pulse signal S.PS able to be provided by the at least one monoflop unit M can be adjustable, in particular between 1 ns and 20 ns, and/or the delay of the adjusted pulse signal S.DS able to be provided by at least one delay unit D can be able to be adjusted.

Figure 2:
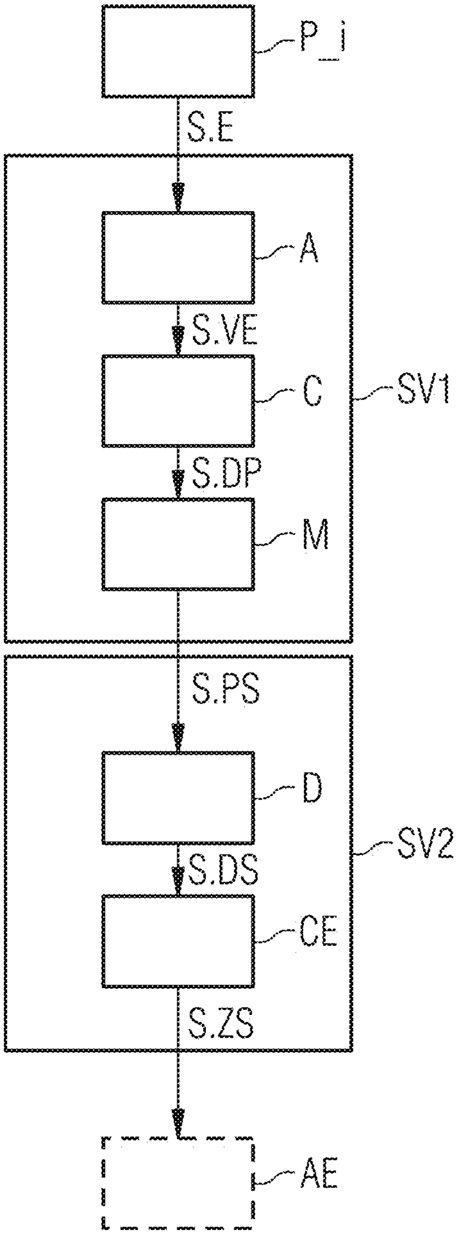

FIG. 2 shows a schematic diagram of a further advantageous form of embodiment of a proposed photon-counting x-ray detector. In this figure the pixel elements, in particular the respective pixel element P_i of the number of pixel elements, in the first signal processing stage SV1 can further each have a signal amplifier A. The signal amplifier A can be embodied to amplify the electrical signal S.E and to provide the amplified electrical signal S.VE to the at least one comparator C.

Figure 3:
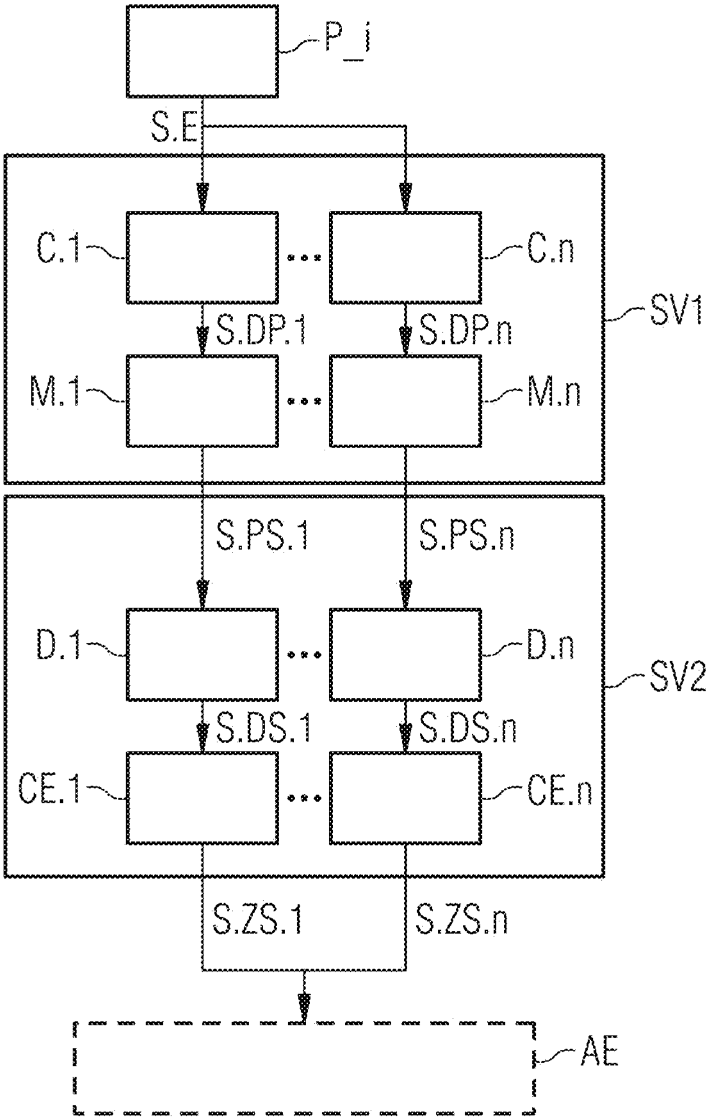

FIG. 3 shows a schematic diagram of a further advantageous form of embodiment of a proposed photon-counting x-ray detector. In this figure the pixel elements, in particular the respective pixel element P_i of the number of pixel elements, in the first signal processing stage SV1 can each have a number of comparators C.1 to C.n and, for at least one of the number of comparators C.1 to C.n, a monoflop unit M.1 to M.n in each case. The comparators C.1 to C.n of a pixel element P_i of the number of pixel elements can each be embodied to compare the electrical signal S.E with various signal threshold values and to provide a digital pixel signal S.DP.1 to S.DP.n in each case depending on the comparison to the respective monoflop unit M.1 to M.n. The monoflop units M.1 to M.n can be embodied, based on the respective digital pixel signal S.DP.1 to S.DP.n, to each provide a pulse signal S.PS.1 to S.PS.n with a defined pulse length to the respective output of the first signal processing stage SV1. The x-ray detector, in the second signal processing stage, for each output of the first signal processing stage, in particular at least for each monoflop unit M.1 to M.n, can have a delay unit D.1 to D.n in each case. The respective delay unit D.1 to D.n can be embodied to provide the respective pulse signal S.PS.1 to S.PS.n with an adjusted delay in each case as an adapted pulse signal S.DS.1 to S.DS.n to the respective counting element CE.1 to CE.n.

Figure 4:
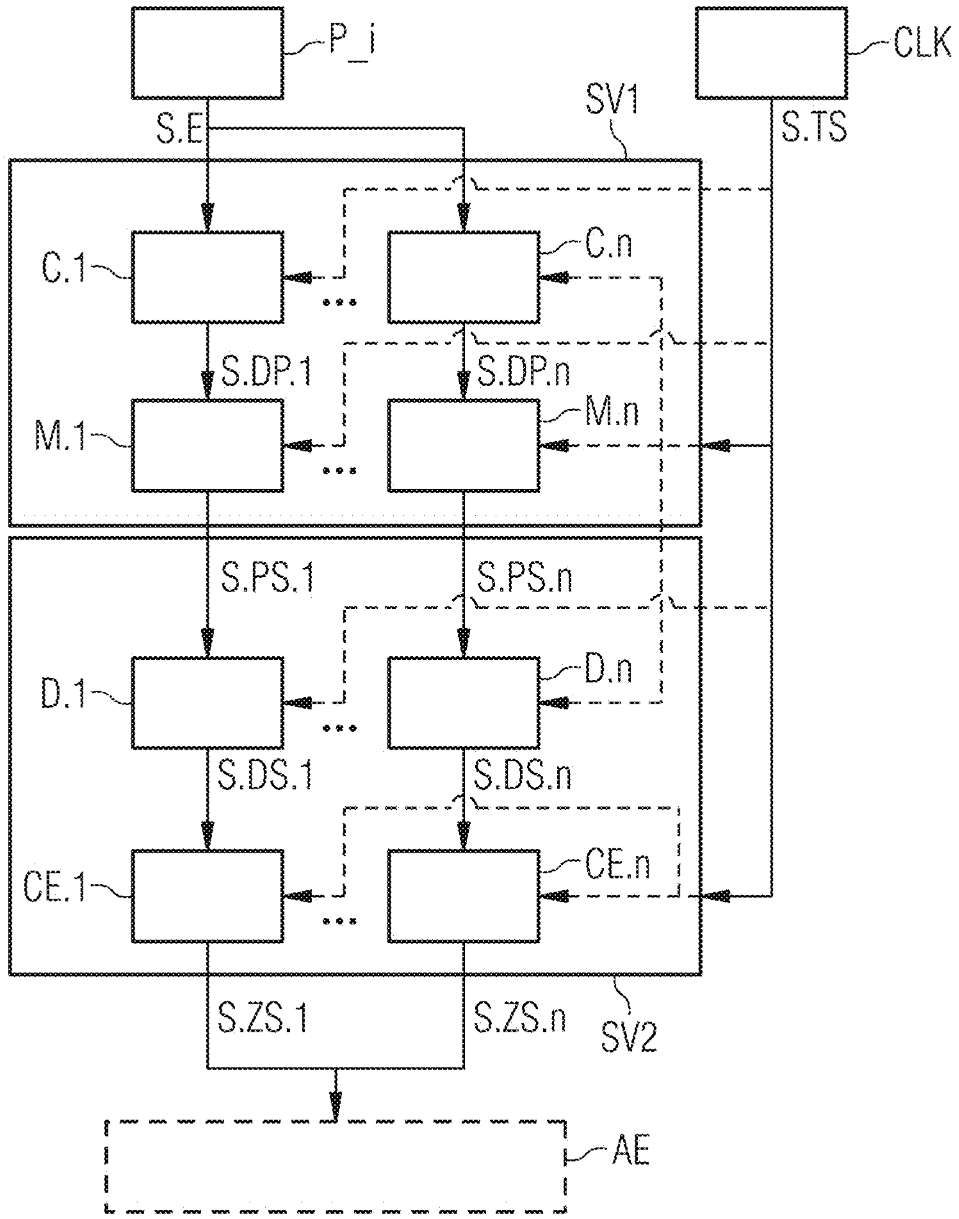

FIG. 4 shows a schematic diagram of a further advantageous form of embodiment of a proposed photon-counting x-ray detector. In this figure the x-ray detector can further have a timing signal generation unit CLK, which is embodied to provide a defined timing signal S.TS to the first signal processing stage SV1, in particular the number of comparators C.1 to C.n, the monoflop units M.1 to M.n, and/or the second signal processing stage SV2, in particular the delay units D.1 to D.n and/or the counting units CE.1 to CE.n. The first signal processing stage SV1 and/or the second signal processing stage SV2 can be embodied to adjust their respective components, which are embodied for time-based processing and/or provision of the respective signals, in particular with the aid of the timing signal S.TS, in particular the number of comparators C.1 to C.n, the monoflop units M.1 to M.n, the delay units D.1 to D.n, and/or the counting units CE.1 to CE.n. The timing signal generation unit CLK can have a number of sub timing signal generation units, which can be embodied to provide a dedicated timing signal for one or for a number of components of the x-ray detector in each case.

Figure 5:
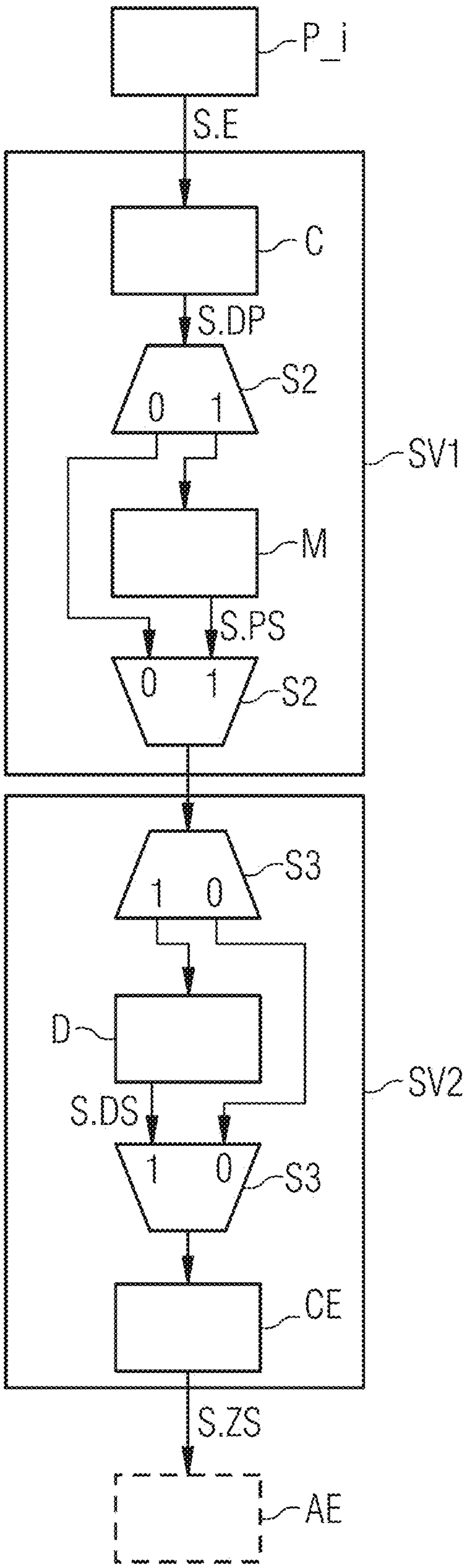

FIG. 5 shows a schematic diagram of a further advantageous form of embodiment of a proposed photon-counting x-ray detector. In this figure the first signal processing stage SV1 can have at least one second switching element S2, which is embodied to activate 1 or to deactivate 0 the at least one monoflop unit M. The second switching element can comprise a demultiplexer and a multiplexer. In this case the at least one comparator C with a deactivated 0 monoflop unit M, can provide the digital pixel signal S.DP to the respective output of the first signal processing stage SV1.

Moreover the first signal processing stage SV1 can have at least one third switching element S3, which is embodied to activate 1 or to deactivate 0 the at least one delay unit D. The third switching element can comprise a demultiplexer and a multiplexer. On deactivation 0 of the at least one delay unit D the signal provided to the respective delay unit D of the at least one delay unit D, in particular the pulse signal S.PS or the digital pixel signal S.DP, can be able to be provided without any delay to the respective counting element CE.

Figure 6:
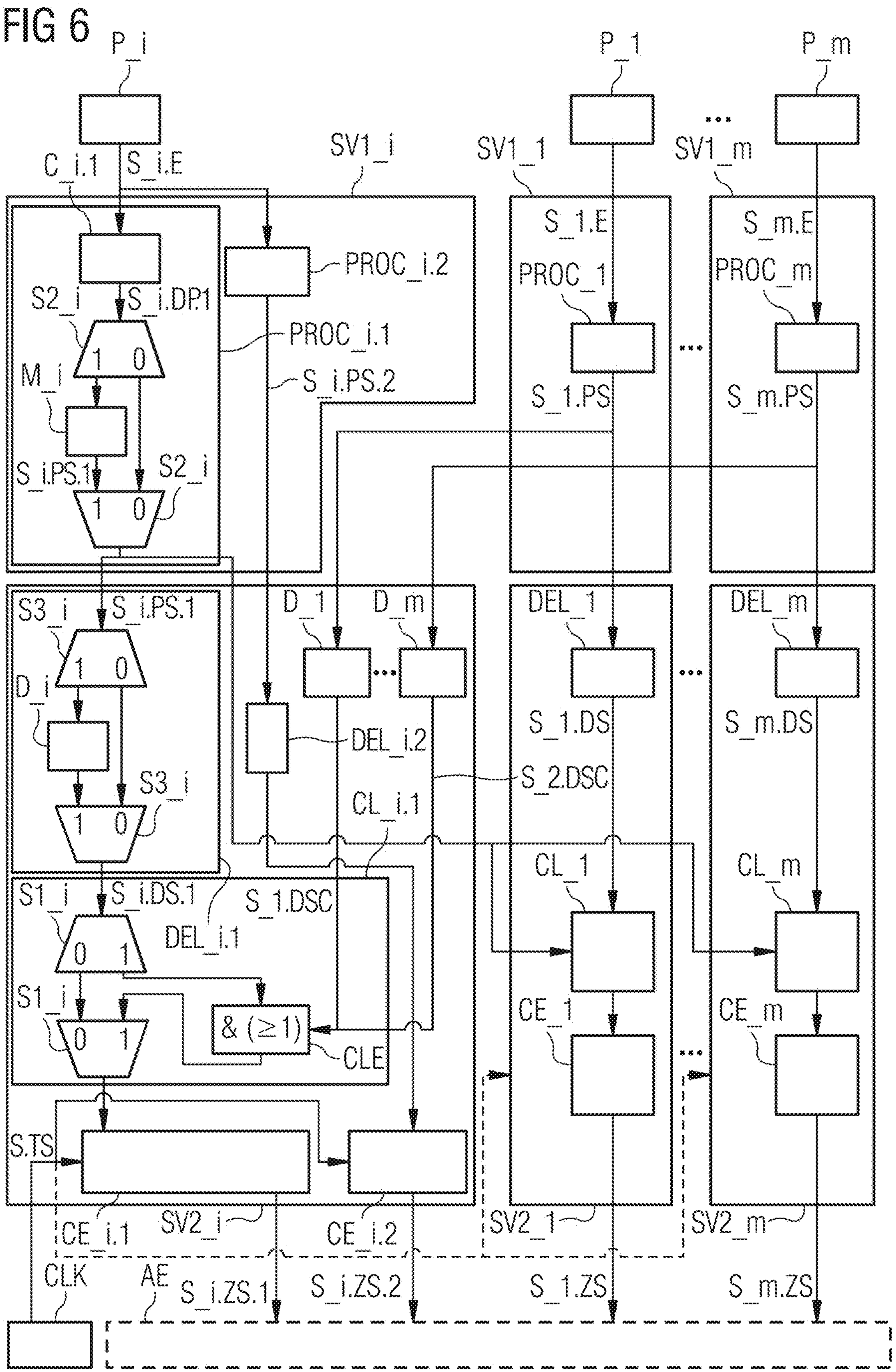

FIG. 6 shows a schematic diagram of a further advantageous form of embodiment of a proposed photon-counting x-ray detector. The first signal processing stages of the respective pixel element P_i and of further pixel elements P_1 to P_m are accordingly labeled with SV1_*i*, SV1_1 to SV1_*m* and the second signal processing stages with SV2_*i*, SV2_1 to SV2_*m*. The respective processing chains for processing the respective electrical signals S_i.E, S_1.E to S_m.E in the respective first signal processing stage SV1_*i*, SV1_1 to SV1_*m* are labeled with PROC_i.1 and PROC_i.2 for the respective pixel element P_i and with PROC_1 to PROC_m for the further pixel elements P_1 to P_m. The processing chains PROC_i.1, PROC_i.2 and PROC_1 to PROC_m can essentially be embodied in a similar manner. The pulse signals S_i.PS_1 and S_i.PS_2 of the respective pixel element P_i and S_1.PS to S_m.PS of the further pixel elements P_1 to P_m able to be provided to the outputs of the respective first signal processing stages, at respective second processing chains DEL_i.1, DEL_i.2 and DEL_1 to DEL_m for delay of the respective signals in the respective second signal processing stage, are labeled SV2_*i* and SV2_1 to SV2_*m*. The processing chains DEL_i.1, DEL_i.2 and DEL_1 to DEL_m can essentially be embodied in a similar manner. The counting elements of the respective pixel elements are further accordingly labeled with CE_i.1 and CE_i.2 for the respective pixel element P_i and with CE_1 to CE_m for the further pixel elements P_1 to P_m. The respective counting signals are labeled with S_i.ZS.1 and S_i.ZS.2 for the respective pixel element P_i and with S_1.ZS to S_m._ZS for the further pixel elements P_1 to P_m.

In the second signal processing stage SV2_*i* of the respective pixel P_i the delay units of at least one group of pixel elements P_i, P_1 to P_m of the number of pixel elements, in particular the at least one delay unit D_i of the respective pixel element P_i and delay units D_1 to D_m of the further pixel elements P_1 to P_m, can be coupled for signaling purposes to a coincidence logic CLE and to a counting element CE_i.1 in each case. The further pixel elements P_1 to P_m, in a similar way to the respective pixel element P_i, can have respective processing chains DEL_1 to DEL_m in their respective second signal processing stage SV2_1 to SV2_*m*. The delay units D_1 to D_m comprised in the second signal processing stage SV2_*i* of the respective pixel element P_i can be different from or the same as the delay units comprised in the respective processing chains DEL_1 to DEL_m.

The, in particular adjusted, pulse signals, S_i.DS.1 and S_1.DSC to S_m.DSC of the at least one group of pixel elements P_i and P_1 to P_m can be able to be provided to the coincidence logic CLE. The coincidence logic CLE can be embodied to identify a coinciding occurrence of adjusted pulse signals S_i.DS.1 of the respective pixel element P_i and adjusted pulse signals S_1.DSC to S_m.DSC of the further pixel elements P_1 to P_m of the at least one group of pixel elements. The at least one counting element CE_i.1 can be embodied, on identification of a coincidence by the coincidence logic CLE, to count a coincidence-counting signal, which is based on the signal arriving directly in the respective pixel element P_i, in particular above the signal threshold values of the comparator C_i.1, and on the coinciding adjusted pulse signal S_1.DSC to S_m. DSC of the further pixel elements P_1 to P_m of the number of pixel elements occurring. The pulse signals S_1.PS to S_m.PS of the further pixel elements can be able to be provided to the coincidence logic via further delay units D_1 to D_m with a respective adjusted delay as the respective adjusted pulse signals S_1.DSC to S_m.DSC. The further pixel elements P_1 to P_m can further have similar first signal processing stages SV1_1 to SV1_*m* and similar second signal processing stages SV2_1 to SV2_*m* to the respective pixel element P_i. The at least one counting element CE_i.1 can be embodied to provide the respective counting signal S_i.ZS.1 based on the first pixel-counting signal and the coincidence-counting signal.

Advantageously the second signal processing stage SV2_*i* of the respective pixel element P_i can have at least one first switching element S1_*i*, which is embodied to activate 1 or to deactivate 0 the coincidence logic CL_i. The first switching element can comprise a demultiplexer and a multiplexer. The counting elements CE_i.1 of the at least one group of pixel elements can count the pixel-counting signal with a deactivated 0 coincidence logic CLE.

The respective processing chains for processing the adjusted pulse signals S_1.DS to S_m.DS of the at least one group of pixel elements, each comprising a coincidence logic CLE and a first switching element, are accordingly labeled in FIG. 6 as CL_i.1 and CL_1 to CL_m.

The respective pixel element P_i, in the first signal processing stage SV1_*i*, can further comprise at least one further processing chain PROC_i.2, which, in particular with respect to the signal threshold values of the respective comparator and/or of the respective monoflop unit, can be different from the first processing chain PROC_i.1 of the respective pixel element P_i.

Advantageously the at least one group of pixel elements can comprise at least one of the pixel elements P_i and at least one further pixel element P_1 to P_m directly adjoining the pixel element P_i in a row or column.

Figure 7:
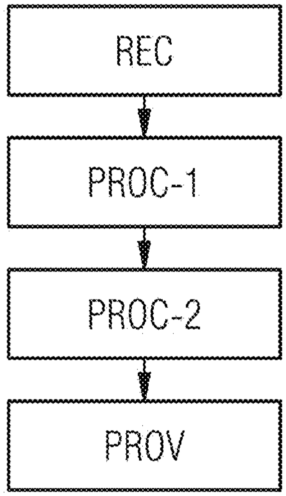
FIGS. 7, 8 and 9 show schematic diagrams of various advantageous forms of embodiment of a proposed method for operating a photon-counting x-ray device.

FIG. 7 shows a schematic diagram of an advantageous form of embodiment of a proposed method for operation of a photon-counting x-ray device. In a first step a), x-ray radiation can be received REC with the photon-counting x-ray detector. In this case the x-ray radiation is converted by the converter element into electrical signals S.E. In a further step b), the electrical signals S.E created by the first signal processing stage SV1 and the second signal processing stage SV2 of the photon-counting x-ray detector are processed PROC-1. In this case the pulse signals S.PS are provided to the outputs of the first signal processing stage SV1, which are further processed PROC-2 by the second signal processing stage SV2. In a further step c), the counting signals S.ZS of the counting elements CE can be provided PROV to the second signal processing stage SV2.

Figure 8:
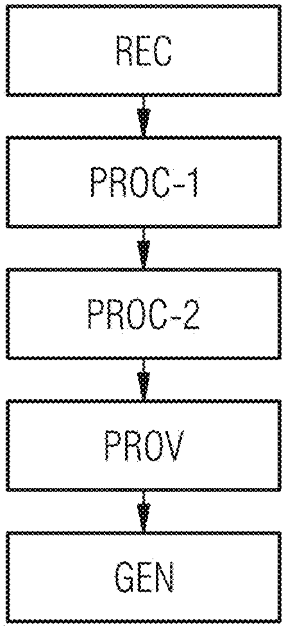

FIG. 8 shows a schematic diagram of a further advantageous form of embodiment of a proposed method for operation of a photon-counting x-ray device. In this case an x-ray image dataset can be generated GEN based on the counting signals S.ZS provided.

Figure 9:
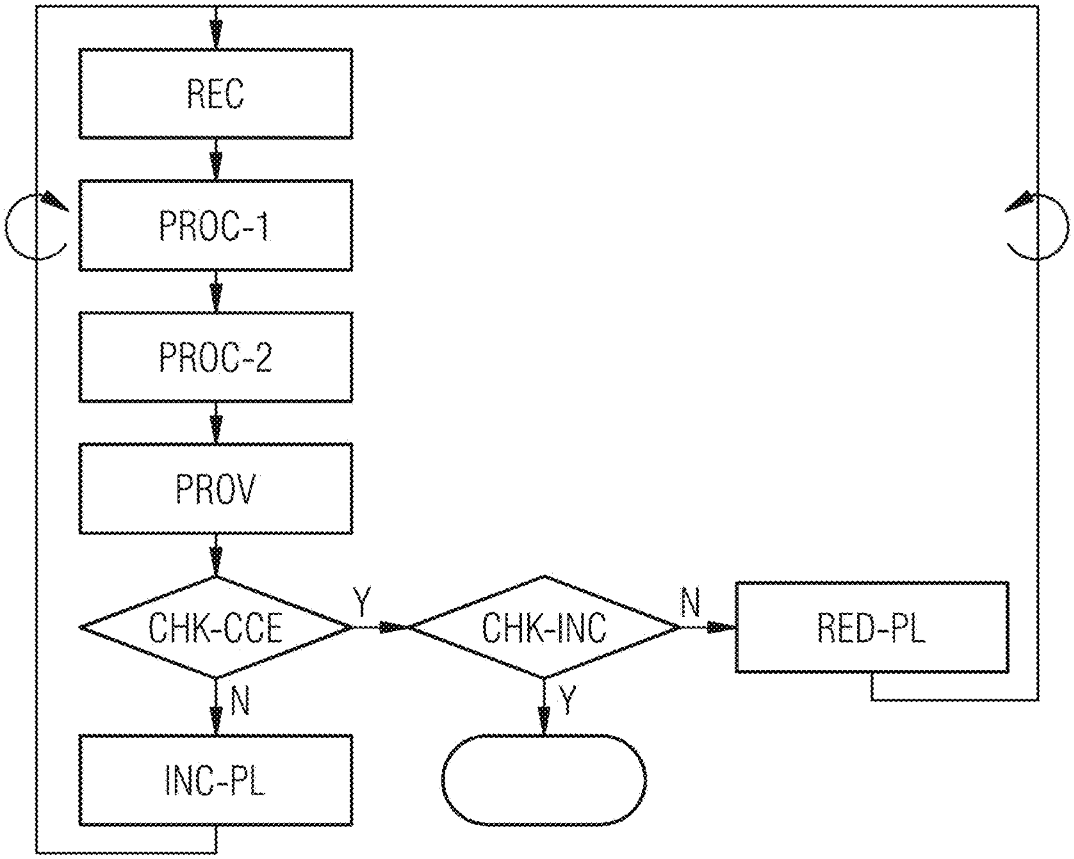

FIG. 9 shows a schematic diagram of a further advantageous form of embodiment of a proposed method for operation of a photon-counting x-ray device. In this case, in step c), a check can be made CHK-CCE as to whether the counting signal S.ZS has a coincidence-counting signal. If it does not N, the defined pulse length is increased INC-PL and the steps a) to c) are repeated. If it does Y, a check can be made CHK-INK, as to whether there has been a previous execution of the steps a) to c) with an increase in the defined pulse length INC-PL. If there has not N, i.e. with no previous increase in the defined pulse length INC-PL, the defined pulse length can be reduced RED-PL and the steps a) to c) can be repeated. Otherwise Y, the method can be ended.

Figure 10:
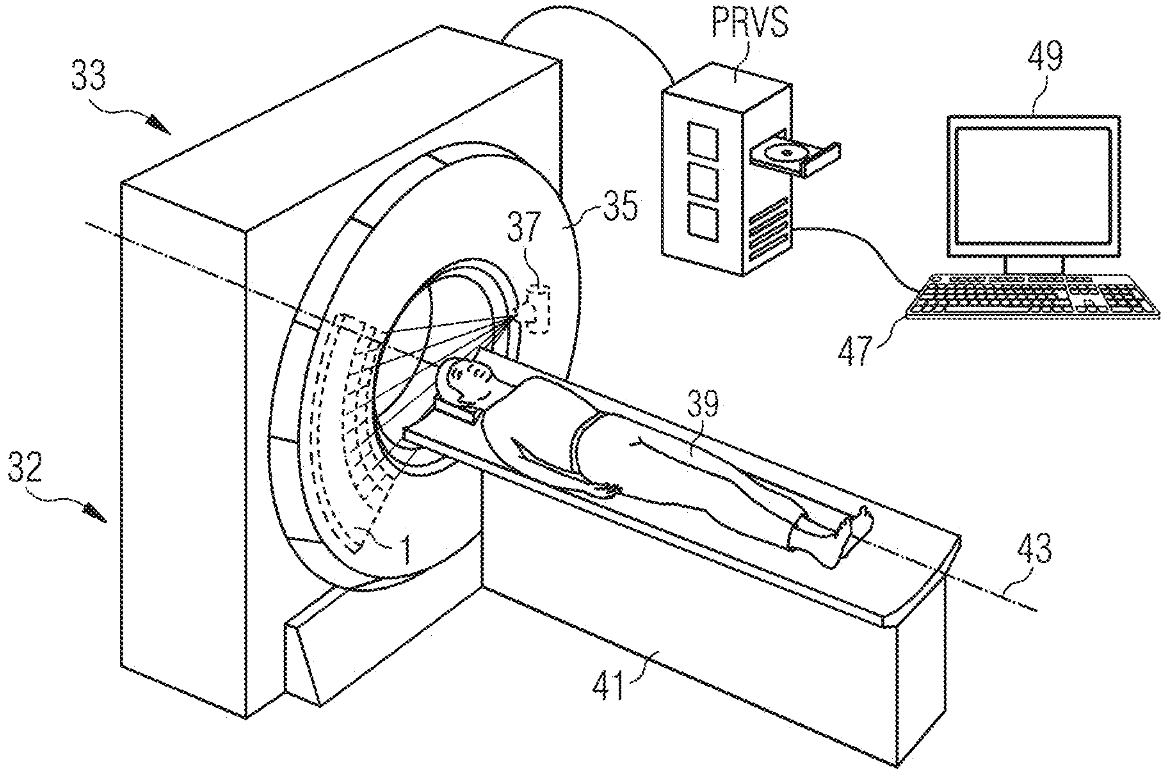
FIG. 10 shows a schematic diagram of a CT device as an example of a form of embodiment of a proposed x-ray device.

FIG. 10 shows a schematic diagram of an advantageous form of embodiment of a proposed x-ray device as a medical CT device 33. The CT device 33 can comprise the x-ray source 37, a proposed photon-counting x-ray detector 1 and a processing unit PRVS. In this figure the x-ray source 37 and the x-ray detector 1 can be arranged opposite one another. The x-ray source 37 can be embodied to illuminate the x-ray detector 1 with x-ray radiation in a direction of incident x-ray radiation. The x-ray detector 1 can comprise a direct-converting (semiconductor) x-ray detector layer. In this case the x-ray detector can for example have CdTe, CdZnTe, CdTeSe, CdZnTeSe or CdMnTe as its semiconductor material.

The CT device 33 can moreover comprise a gantry 32 with a rotor 35. The x-ray source 37 and the x-ray detector 1 can be arranged in a defined arrangement on the rotor 35, in particular integrated into the rotor 35 or attached to the rotor 35. The rotor 35 can be supported rotatably about an axis of rotation 43. The examination object 39 to be imaged can be supported on the patient support apparatus 41 and be able to be moved along the axis of rotation 43 through the gantry 32. The processing unit PRVS can be used for control of the CT device 33 and for calculations of slice images or volume images of the examination object 39. An input facility 47, for example a keyboard, and an output facility 49, for example a screen and/or display, can be connected to the processing unit PRVS, in particular coupled to it for signaling purposes. The input facility 47 can advantageously be integrated into the output facility 49, for example into an, in particular resistive and/or capacitive, input display. The output facility 49 can be embodied for display of a graphical representation of the counting signals and/or of the x-ray image dataset.

The schematic representations contained in the figures described do not depict any sort of scale or size relationships.

It is pointed out in conclusion that the method described in detail above, as well as the apparatuses shown, merely involve exemplary embodiments, which can be modified by the person skilled in the art in a very wide variety of ways without departing from the field of the present invention. Furthermore the use of the indefinite article "a" or "an" does not exclude the features concerned also being able to be present a number of times. Likewise the terms "unit" and "element" do not exclude the components concerned consisting of a number of interacting part components, which where necessary can also be spatially distributed.

The expression "based on" can be understood in the context of the present application in particular in the sense of the expression "using". In particular a formulation according to which a first feature is created (alternatively: established, determined etc.) based on a second feature, does not exclude that the first feature can be created (alternatively: established, determined etc.) based on a third feature.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as “processing” or “computing” or “calculating” or “determining” of “displaying” or the like, refer to the action and processes of a computer system, or similar electronic computing device/hardware, that manipulates and transforms data represented as physical, electronic quantities within the computer system’s registers and memories into other data similarly represented as physical quantities within the computer system memories or registers or other such information storage, transmission or display devices.

In this application, including the definitions below, the term ‘module’ or the term ‘controller’ may be replaced with the term ‘circuit.’ The term ‘module’ may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

What is claimed is:

1. A photon-counting x-ray detector, comprising:

a number of pixel elements;

a converter element for conversion of x-ray radiation into electrical signals;

a first signal processing stage for each respective pixel element of the number of pixel elements, the first signal processing stage including at least one comparator and at least one monoflop unit, wherein the at least one comparator is configured to compare an electrical signal from a pixel element with a signal threshold value, and provide a digital pixel signal to the at least one monoflop unit based on the comparison, the at least one monoflop unit is configured to, based on the digital pixel signal, provide a pulse signal with a defined pulse length to an output of the first signal processing stage;

a second signal processing stage for each respective pixel element of the number of pixel elements, the second signal processing stage including at least one delay unit and at least one counting element, wherein each respective output of the first signal processing stage is coupled to a respective delay unit for signaling purposes, each delay unit is configured to provide a pulse signal with a respective adjusted delay, as a respective adjusted pulse signal, to a respective counting element, wherein the respective adjusted delay is based on a circuit-related delay of a respective pixel element of the number of pixel elements, and each counting element is configured to count a counting signal based on the respective adjusted pulse signal.

2. The photon-counting x-ray detector as claimed in claim 1, wherein the first signal processing stage further includes a signal amplifier, and wherein the signal amplifier is configured to amplify the electrical signal and provide the amplified electrical signal to the at least one comparator.

3. The photon-counting x-ray detector as claimed in claim 1, wherein the at least one monoflop unit is configured to provide the pulse signal upon identifying a rising edge of the digital pixel signal.

4. The photon-counting x-ray detector as claimed in claim 1, wherein the first signal processing stage includes a number of comparators and a number of corresponding monoflop units, wherein each comparator is configured to compare the electrical signal with a respective signal threshold value, and provide a respective digital pixel signal to a corresponding monoflop unit based on the comparison, and wherein the corresponding monoflop unit is configured to, based on the respective digital pixel signal, provide a pulse signal with a defined pulse length to a respective output of the first signal processing stage.

5. The photon-counting x-ray detector as claimed in claim 1, wherein the second signal processing stage includes a number of delay units for at least one group of pixel elements of the number of pixel elements, each delay unit being coupled, for signaling purposes, to a coincidence logic and to a respective counting element, wherein adjusted pulse signals for the at least one group of pixel elements are configured to be provided to the coincidence logic, wherein the coincidence logic is configured to identify a coinciding occurrence of adjusted pulse signals of pixel elements, wherein respective counting elements of the at least one group of pixel elements are configured to count a pixel-counting signal, which is based on a signal arriving directly in pixel elements of the at least one group of pixel elements, or based on identification of a coincidence by the coincidence logic, count a coincidence-counting signal, which is based on the pixel-counting signal arriving directly in the respective pixel element and is based on a coinciding occurring signal of at least one further pixel element of the number of pixel elements.

6. The photon-counting x-ray detector as claimed in claim 5, wherein the second signal processing stage includes at least one first switching element configured to activate or deactivate the coincidence logic, and wherein the respective counting elements, of the at least one group of pixel elements, are configured to count the pixel-counting signal when the coincidence logic is deactivated.

7. The photon-counting x-ray detector as claimed in claim 5, wherein the at least one group of pixel elements comprises at least one pixel element and at least one further pixel element directly adjoining the at least one pixel element in a row or column.

8. The photon-counting x-ray detector as claimed in claim 1, further comprising:

a clock signal generation unit configured to provide a timing signal to at least one of the first signal processing stage or the second signal processing stage, and wherein the at least one of the first signal processing stage or the second signal processing stage is configured to adjust respective components included therein, the respective components configured for at least one of time-based processing or time-based provision with the aid of the timing signal.

9. The photon-counting x-ray detector as claimed in claim 1, wherein the first signal processing stage includes at least one second switching element configured to activate or to deactivate the at least one monoflop unit, and wherein the at least one comparator provides the digital pixel signal to the respective output of the first signal processing stage when the at least one monoflop unit is deactivated.

10. The photon-counting x-ray detector as claimed in claim 1, wherein the second signal processing stage includes at least one third switching element, which is configured to activate or to deactivate the at least one delay unit, and wherein, on deactivation of the at least one delay unit, the pulse signal is provided to the respective counting element without any delay.

11. The photon-counting x-ray detector as claimed in claim 1, wherein at least one of the defined pulse length is between 1 ns and 20 ns, or the respective adjusted delay of is adjustable.

12. A method for operation of the photon-counting x-ray detector of claim 1, the method comprising:

receiving x-ray radiation at the photon-counting x-ray detector;

converting the x-ray radiation into the electrical signals by the converter element;

processing the electrical signals by the first signal processing stage and the second signal processing stage, wherein pulse signals are provided to outputs of the first signal processing stage, and the pulse signals are further processed by the second signal processing stage; and provisioning counting signals to the counting elements of the second signal processing stage.

13. The method as claimed in claim 12, wherein an x-ray image dataset is generated based on the counting signals.

14. The method as claimed in claim 12, wherein the provisioning comprises:

checking whether a counting signal has a coincidence-counting signal;

increasing the defined pulse length and repeating the receiving, converting, processing and provisioning, in response to the counting signal not having a coincidence counting signal; and reducing the defined pulse length and repeating the receiving, converting, processing and provisioning in response to the counting signal having a coincidence counting signal and there having been no previous increase in the defined pulse length.

15. An x-ray device, comprising:

an x-ray source; and the photon-counting x-ray detector as claimed in claim 1, wherein the x-ray source is configured to emit x-ray radiation for illumination of the photon-counting x-ray detector.

16. The photon-counting x-ray detector as claimed in claim 2, wherein the at least one monoflop unit is configured to provide the pulse signal upon identifying a rising edge of the digital pixel signal.

17. The photon-counting x-ray detector as claimed in claim 3, wherein the first signal processing stage includes a number of comparators and a number of corresponding monoflop units, wherein each comparator is configured to compare the electrical signal with a respective signal threshold value, and provide a respective digital pixel signal to a corresponding monoflop unit based on the comparison, and wherein the corresponding monoflop unit is configured to, based on the respective digital pixel signal, provide a pulse signal with a defined pulse length to a respective output of the first signal processing stage.

18. The photon-counting x-ray detector as claimed in claim 4, wherein the second signal processing stage includes a number of delay units for at least one group of pixel elements of the number of pixel elements, each delay unit being coupled, for signaling purposes, to a coincidence logic and to a respective counting element, wherein adjusted pulse signals for the at least one group of pixel elements are configured to be provided to the coincidence logic, wherein the coincidence logic is configured to identify a coinciding occurrence of adjusted pulse signals of pixel elements, wherein respective counting elements of the at least one group of pixel elements are configured to count a pixel-counting signal, which is based on a signal arriving directly in pixel elements of the at least one group of pixel elements, or based on identification of a coincidence by the coincidence logic, count a coincidence-counting signal, which is based on the pixel-counting signal arriving directly in the respective pixel element and is based on a coinciding occurring signal of at least one further pixel element of the number of pixel elements.

19. The photon-counting x-ray detector as claimed in claim 6, wherein the at least one group of pixel elements comprises at least one pixel element and at least one further pixel element directly adjoining the at least one pixel element in a row or column.

20. The photon-counting x-ray detector as claimed in claim 9, wherein the second signal processing stage includes at least one third switching element, which is configured to activate or to deactivate the at least one delay unit, and wherein, on deactivation of the at least one delay unit, the pulse signal is provided to the respective counting element without any delay.

* * * * *